(12) United States Patent
Hesse et al.

(10) Patent No.: US 7,056,855 B1
(45) Date of Patent: Jun. 6, 2006

(54) LIQUID TETRABUTYL AMMONIUM PHENOLATE FORMULATION

(75) Inventors: Carsten Hesse, Tönisvorst (DE); Ursula Jansen, Neuss (DE); Johann Rechner, Kapellen (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/868,489

(22) PCT Filed: Dec. 9, 1999

(86) PCT No.: PCT/EP99/09689

§ 371 (c)(1),
(2), (4) Date: Jun. 18, 2001

(87) PCT Pub. No.: WO00/37402

PCT Pub. Date: Jun. 29, 2000

(30) Foreign Application Priority Data

Dec. 21, 1998 (DE) ................ 198 58 967

(51) Int. Cl.
*B01J 31/00* (2006.01)

(52) U.S. Cl. .................................... 502/164

(58) Field of Classification Search ............ 502/164
See application file for complete search history.

(56) References Cited

U.S. PATENT DOCUMENTS

| | | | |
|---|---|---|---|
| 3,833,572 A | 9/1974 | Clark et al | 260/243 C |
| 4,830,785 A | 5/1989 | Shinozaki et al. | 252/62.2 |
| 5,495,038 A * | 2/1996 | Buysch et al. | 558/274 |
| 5,502,232 A * | 3/1996 | Buysch et al. | 558/270 |
| 5,739,257 A * | 4/1998 | Boden et al. | 528/196 |
| 6,177,538 B1 * | 1/2001 | Hesse et al. | 528/219 |
| 6,207,848 B1 * | 3/2001 | Pressman | 558/274 |
| 6,338,822 B1 * | 1/2002 | Waldner et al. | 422/82.07 |
| 6,734,325 B1 * | 5/2004 | Reisinger et al. | 564/296 |
| 6,740,781 B1 * | 5/2004 | Fischer et al. | 564/230 |

FOREIGN PATENT DOCUMENTS

| | | |
|---|---|---|
| EP | 0362854 | 4/1990 |
| WO | WO0037402 A1 * | 6/2000 |

OTHER PUBLICATIONS

Journal of the Chemical Society, Faraday Transactions, GB, Royal Society of Chemistry, Cambridge, Bd. 89, Nr. 1, 1993, Seiten 119-122, XP0000867637, ISSN: 0956-5000, in der Anmeldung erwähnt, J. Magonski et al, "Dissociation Constants of Substituted Phenols and Homoconjugation Constants of the Corresponding Phenol-Phenolate Systems in Acetonitrile".

Inorganic Chemistry, vol. 25, Oct.-Dec., 1985, pp. 3311-4830, T. J. McNeese et al, "Synthesis and Characterization of Polynuclear Chromium Carbonyl Tetraanions".

J. Am. Chem. Soc., (month unavailable), 1983, vol. 105, pp. 475-483, P. K. Mascharak et al, Single Cubane-Type $MFe_3S_4$ Clusters (M=Mo, W): Synthesis and Properties of Oxidized and Reduced Forms and the Structure of $(Et_4N)_3[MoFe_3S_4(S-p-C_6H_4CL)_4(3,6-(C_3H_5)_2C_6H_2O_2)]$.

* cited by examiner

*Primary Examiner*—J. A. Lorengo
*Assistant Examiner*—Jennine Brown
(74) *Attorney, Agent, or Firm*—Joseph C. Gil; Aron Preis

(57) ABSTRACT

A process for preparing a formulation containing tetrabutylammonium phenolate and phenol is disclosed. The process entails combining a solution of tetrabutylammonium bromide in phenol with a solution of sodium phenolate to form a mixture, excess phenol is removed by distillation, and sodium bromide is filtered off. The formulation, that contains tetrabutylammonium phenolate and phenol in a weight ratio of 40:60 to 70:30, has a solidification point of less than 25° C. and finds use as a catalyst constituent.

9 Claims, No Drawings

LIQUID TETRABUTYL AMMONIUM PHENOLATE FORMULATION

The present invention relates to a formulation of tetrabutylammonium phenolate that is liquid at room temperature, and to processes for its preparation.

Various tetraalkylammonium phenolates have already become known. For example, J. Am. Chem. Soc. 103 (1983) 475 and Inorg. Chem. 24 (1985) 3465 disclose the preparation of tetraethylammonium phenolate; the preparation of tetrabutylammonium phenolate is known from DE-OS 22 03 448; and EP-A 244 799 teaches the preparation of an electrolyte containing tetraalkylammonium phenolates.

Various phenol adducts of tetraalkylammonium phenolates have also already become known. J. Chem. Soc. Faraday Trans. 89 (1993) 119 discloses the preparation of (mono)phenol adducts of various tetraalkylammonium phenolates, and the preparation of the di(p-tert-butylphenol) adduct of tetrabutylammonium (p-tert-butylphenolate) is disclosed in EP-A 362 854.

All those compounds are substances that are solid at room temperature. For large-scale application, however, it is desirable to have available a formulation that is liquid at room temperature, since metering is greatly simplified thereby.

The invention provides formulations containing tetrabutylammonium phenolate (TBAP) and phenol in a weight ratio of from 40:60 to 70:30, preferably from 50:50 to 60:40, and having a solidification point of <25° C., preferably <20° C.

The invention also provides processes for the preparation of the formulations according to the invention. The formulations according to the invention can be prepared by first dissolving sodium phenolate and tetrabutylammonium bromide (TBAB) separately at temperatures of >40° C. in phenol. When the two phases are brought together, sodium bromide is immediately formed as a fine precipitate.

Excess phenol is removed by distillation under reduced pressure until the desired mixing ratio of TBAP and phenol is achieved.

After cooling to room temperature, sodium bromide is separated off from the cloudy liquid. That can be effected by the conventional methods known to the person skilled in the art, for example by filtration, sedimentation or centrifugation. Separation of the precipitate is preferably carried out by filtration. In an especially preferred embodiment, the filtration is carried out over a pressure suction filter having a filter mat for finely dispersed materials (deep-bed filtration). The sodium content of the filtered solution is lower, the finer the filter used. If filter mats having retention rates of <40 μm are used, formulations containing less than 1000 ppm sodium ions can be obtained.

Since sodium phenolate is relatively poorly soluble in phenol, a large excess of phenol must first be used, which must later be removed again. In a preferred embodiment of the process according to the invention, therefore, sodium phenolate is dissolved in a small amount of water and added to a solution of tetrabutylammonium bromide in phenol. The water is subsequently removed by distillation as an azeotropic mixture with phenol. In that variant, only about one tenth of the amount of phenol that is required for preparation via sodium phenolate solutions in phenol is required to prepare the formulations according to the invention. Moreover, the sodium contents of the resulting solutions are markedly lower, with values of <500 ppm.

The formulations according to the invention are preferably used as a constituent of catalyst systems, for example for the production of phenol resins. Accordingly, the invention relates also to the use of the formulations according to the invention as a catalyst constituent.

EXAMPLES

Salts having a water content of <500 ppm were used. The water content of the products was determined by means of Karl-Fischer titration, the bromide content was determined by argentometry, and the sodium content was determined by ICP.

Example 1

In a 250 ml two-necked flask having a Vigreux column and a distillation bridge, a magnetic stirrer bead and a glass stopper, 36.8 g (0.11 mol) of TBAB were added to 36.8 g (0.39 mol) of molten phenol, and the mixture was allowed to cool to room temperature (solution A). In a 250 ml glass beaker, 19.4 g (0.11 mol) of sodium phenolate trihydrate were dissolved in 30 ml of water (solution B).

Solution A was then added dropwise to B in the course of 15 minutes at 60° C., with rapid stirring. Finally, 43 g of molten phenol were added. Approximately 64 g of that mixture were distilled off in vacuo. The residue consisted of a dark brown liquid with a fine beige-coloured sediment, which was filtered off over a pressure suction filter lined with a filter mat having a retention rate of 15–35 μm (T2100, Seitz Filterwerke GmbH, D-55543 Bad Kreuznach).

The sodium content was 250 ppm, the bromide content was 0.21 wt. %.

Example 2

The procedure was analogous to Example 1, but a filter mat having a retention rate of 25–70 μm (T5500, Seitz Filterwerke GmbH, D-55543 Bad Kreuznach) was used for the filtration.

The sodium content was 1600 ppm, the bromide content was 0.38 wt. %.

Example 3

In a 1 liter three-necked flask, 19.4 g (0.11 mol) of sodium phenolate trihydrate were dissolved in 600 g (6.4 mol) of phenol (solution A). In a 100 ml glass beaker, 36.75 g (0.11 mol) of TBAB were dissolved in 36.75 g (0.39 mol) of phenol, while heating, and the mixture was then allowed to cool to room temperature (=solution B).

Solution B was added to solution A, and excess phenol was removed by distillation in vacuo at an internal temperature of 60° C. until a molar ratio of TBAP:PhOH of approximately 1:8 was achieved. The sodium bromide that had formed was filtered off over a pressure suction filter with a filter mat having a retention rate of 15–35 μm (T2100, Seitz Filterwerke GmbH, D-55543 Bad Kreuznach).

The sodium content was 700 ppm, the bromide content was 0.21 wt. %.

Example 4

In a 1 liter three-necked flask, 19.4 g (0.11 mol) of sodium phenolate trihydrate were dissolved in 30 ml of water (solution A). In a 100 ml glass beaker, 36.75 g (0.11 mol) of TBAB were dissolved in 36.75 g (0.39 mol) of phenol, while heating, and the mixture was then allowed to cool to room temperature (=solution B).

Solution B was added to solution A, and water and excess phenol were removed by distillation in vacuo at an internal temperature of 60° C. until a weight ratio of TBAP to phenol of approximately 1:1 was achieved. The sodium bromide that had formed was filtered off over a pressure suction filter with a filter mat having a retention rate of 15–35 μm (T2100, Seitz Filterwerke GmbH, D-55543 Bad Kreuznach).

The sodium content was 250 ppm, the bromide content was 0.21 wt. %, and the water content was 800 ppm.

Example 5

Example 4 was repeated, but the reaction mixture was stirred at 60° C. for 16 hours before being filtered.

The sodium content of the filtrate was 180 ppm, the bromide content was 0.18 wt. %, and the water content was 900 ppm.

The invention claimed is:

1. Formulations containing tetrabutylammonium phenolat and phenol in a weight ratio of from 40:60 to 70:30 and having a solidification point of <25° C.

2. Process for the preparation of the formulations according to claim 1, in which solutions of tetrabutylammonium bromide and sodium phenolate in phenol are combined, excess phenol is removed from the mixture by distillation, and sodium bromide is then filtered off.

3. Process for the preparation of the formulations according to claim 1, in which a solution of tetrabutylammonium bromide in phenol and an aqueous solution of sodium phenolate are combined, water and excess phenol are removed from the mixture by distillation, and sodium bromide is then filtered off.

4. Process for the preparation of the formulations according to claim 1, in which solutions of tetrabutylammonium bromide and sodium phenolate trihydrate in phenol are combined, water and excess phenol are removed from the mixture by distillation, and sodium bromide is then filtered off.

5. A process for preparing a formulation containing tetrabutylammonium phenolate and phenol comprising combining a solution of tetrabutylammonium bromide in phenol with a solution of sodium phenolate in phenol to form a mixture, removing from the mixture excess phenol by distillation, and filtering off sodium bromide, said tetrabutylammonium phenolate and phenol being present in said formulation in a weight ratio of 40:60 to 70:30, said formulation having a solidification point of less than 25° C.

6. The formulation prepared by the process of claim 5.

7. A catalyst comprising the formulation of claim 6.

8. A process for preparing a formulation containing tetrabutylammonium phenolate and phenol comprising combining a solution of tetrabutylammonium bromide in phenol with an aqueous solution of sodium phenolate to form a mixture, removing from the mixture water and excess phenol distillation, and filtering off sodium bromide, said tetrabutylammonium phenolate and phenol being present in said formulation in a weight ratio of 40:60 to 70:30, said formulation having a solidification point of less than 25° C.

9. A process for preparing a formulation containing tetrabutylammonium phenolate and phenol comprising combining a solution of tetrabutylammonium bromide in phenol with a solution of sodium phenolate trihydrate in phenol to form a mixture, removing from the mixture water and excess phenol by distillation, and filtering off sodium bromide, said tetrabutylammonium phenolate and phenol being present in said formulation in a weight ratio of 40:60 to 70:30, said formulation having a solidification point of less than 25° C.

* * * * *